United States Patent [19]

Welker

[11] Patent Number: 4,463,603

[45] Date of Patent: Aug. 7, 1984

[54] VOLUME ANALYZER FOR CRUDE OIL SAMPLING SYSTEM INCLUDING BITE CHECKING APPARATUS

[75] Inventor: Robert H. Welker, Sugar Land, Tex.

[73] Assignee: Welker Engineering Company, Sugar Land, Tex.

[21] Appl. No.: 460,480

[22] Filed: Jan. 24, 1983

[51] Int. Cl.³ .............................................. G01M 19/00
[52] U.S. Cl. ......................................... 73/168; 73/239; 73/864.62; 138/31
[58] Field of Search .................... 138/31, 104; 73/239, 73/863, 168

[56] References Cited

U.S. PATENT DOCUMENTS

| | | |
|---|---|---|
| 769,161 | 9/1904 | Houston . |
| 1,844,843 | 2/1932 | Dezendorf . |
| 2,637,211 | 5/1953 | Norman .......................... 73/864.62 |
| 2,826,067 | 3/1958 | Braunlich ............................ 73/168 |
| 2,934,938 | 5/1960 | Rhoades ................................ 73/3 |
| 2,970,474 | 2/1961 | Kendig .................................. 73/112 |
| 3,768,510 | 10/1973 | Reves ................................ 137/551 |
| 3,939,688 | 2/1976 | Misch ...................................... 73/3 |
| 4,171,638 | 10/1979 | Coman ................................ 73/119 |
| 4,409,850 | 10/1983 | Zeck ................................ 73/864.62 |

*Primary Examiner*—S. Clement Swisher
*Attorney, Agent, or Firm*—Gunn, Lee & Jackson

[57] ABSTRACT

For use in a crude oil sampling system which delivers samples in pumped pulse fashion, a volumetric analyzer accumulating the sample is disclosed. In the preferred and illustrated embodiment, the device incorporates a valve which is selectively closed to direct the pumped pulsed sample into the apparatus. It includes a cylinder head attached to a cylinder. In the cylinder, there is a reducer sleeve. The reducer sleeve encloses a piston of selected size. The piston is forced upwardly by sample introduced beneath it. The piston connects with a push rod which in turn extends from the apparatus and which supports a piston follower having a marker cooperative with a scale to indicate the volumetric accumulation below the piston. The piston and reducer sleeve calibrate the apparatus to selected maximum capacities.

11 Claims, 1 Drawing Figure

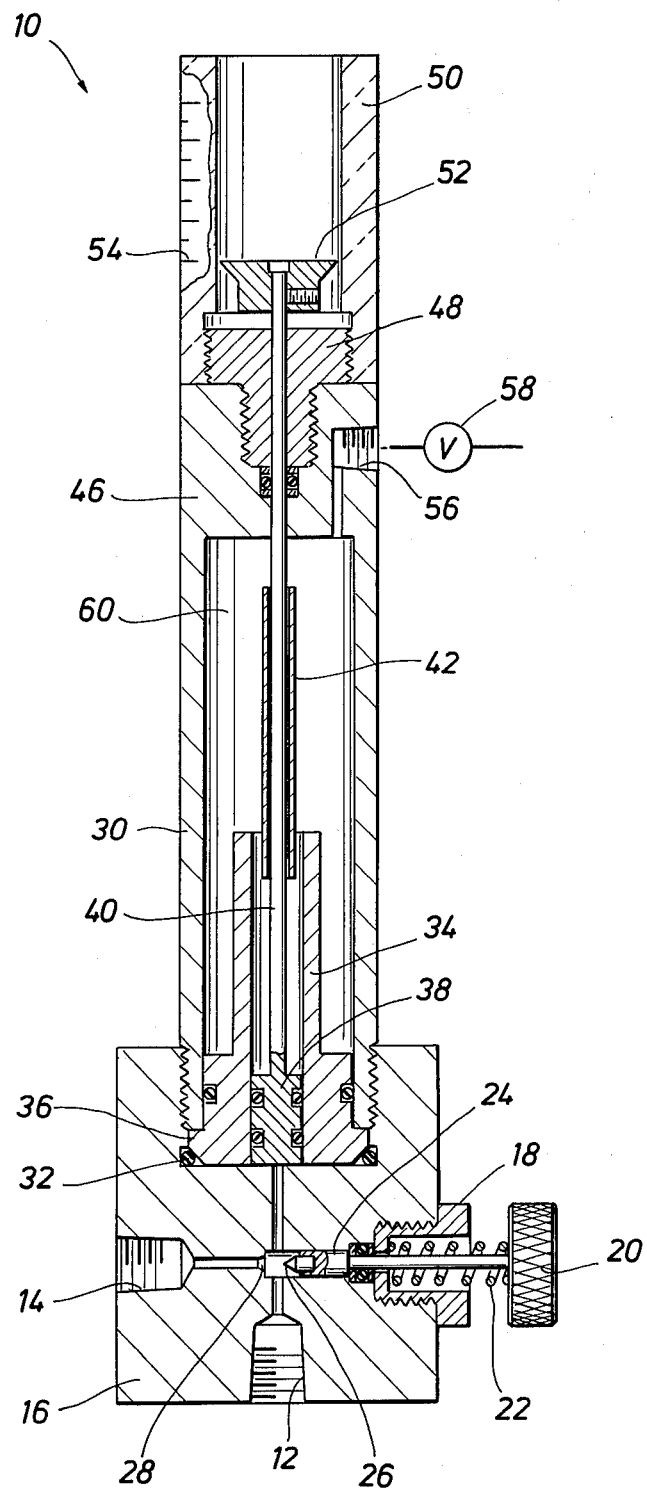

VOLUME ANALYZER FOR CRUDE OIL SAMPLING SYSTEM INCLUDING BITE CHECKING APPARATUS

BACKGROUND OF THE DISCLOSURE

This disclosure is directed to sample checking apparatus for use with a crude oil sampling system. It also can be used with pulsed chemical injectors. These devices are characterized by pulsating pumped samples periodically delivered from the pump apparatus. For instance, the device that is upstream of the present apparatus may pump samples at the rate of one sample every minute, each sample being 50 cubic centimeters. Interruption of the sample flow is undesirable. For this reason, it is benefical to check whether or not the sampling apparatus is operative, and to measure the cumulative volume of samples over a period of time. This apparatus enables chemical injectors or sampling apparatus to be checked. It particularly enables such a device to be gauged to further determine if the sum of samples over a period of time measures the desired volume. For instance, for a measured time interval, the desired sample volume might total 500 cubic centimeters, and it is desirable to test to determine accuracy of volumetric output for the specified interval. Whatever the case, this apparatus is highly useful in testing, and it is particularly benficial to determine volumetric flow. It is useful to determine volumetric flow for specific interval so that proper operation of the system can be verified.

With this in view, the present apparatus is described in brief as a bite checking apparatus adapted to be connected downstream from a chemical injector or crude oil sampling device. It cooperates with an upstream device which furnishes samples of fixed size periodically. It particularly finds use with a sampling system which takes a sample from a large flow as might be observed in a pipeline. The sample is delivered to the apparatus and is accumulated temporarily in it. This apparatus is adapted to be changed in size and hence, storage capacity. This will be noted in the details of description hereinbelow. The apparatus incorporates a cylinder head having a diverter valve therein. The apparatus is switched off by means of a manually operated push valve. When it is to be operated, the push valve is switched, thereby diverting the flow into the apparatus. The cylinder head supports the manual push valve, a suitable valve structure, and a flow path through the apparatus. The head also supports a cylinder. The cylinder encloses a reducer sleeve. The reducer sleeve encloses a piston which is sized to define a particular capacity chamber. The piston is thus located within the reducer. The piston is connected with a piston rod which extends upwardly. The top face of the piston is exposed to compress gas within the cylinder. This serves as a return spring. The cylinder encloses the reducer with the piston rod forced axially upwardly through the top end of the cylinder. There, the rod connects with a piston follower. The piston follower is surrounded by a housing which supports a visable scale marked on the housing, preferably formed of a transparent material with scale marks thereon.

This apparatus is particularly adapted to be sized by utilization of different pistons and reducers within the cylinder. The cross-sectional area can be modified. Alternately, the piston follower and associated scale can be scaled differently to accomodate changes in scale.

BRIEF DESCRIPTION OF THE DRAWING

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

The single drawing is a sectional view through the apparatus of the present disclosure setting forth details of construction.

DETAILED DESCRIPTION OF THE PREFERRED EMBODIMENT

Attention is first directed to the single drawing where the bite check measuring apparatus is identified by the numeral 10. It is threaded at the tapped inlet fitting 12 to connect with an upstream chemical injector or sampling apparatus. The system further includes a similar threaded or tapped fitting 14 which connects to a downstream receptacle for receiving the sample. The tapped holes 12 and 14 are formed in a cylinder head block 16. The cylinder head 16 is constructed of an upstanding right cylinder body. Passages are drilled through it to enable connection the tapped openings 12 and 14. For instance, it is drilled transversely across the body at a diameter, thereby enabling the port 14 to be countersunk and tapped from the left. In like fashion, this passage is countersunk from the right to enable a threaded nut 18 to be fitted at the right end used to secure a manual push valve 20 in position.

The push valve 20 incorporates an elongate valve stem 22. The stem 22 passes through the smaller end of the nut 18 to support an enlargement 24 sized to fit within the passage surrounding it, and the enlargement supports a pointed valve element 26. The valve element 26 is sized to plug the passage 28, thereby preventing flow to the outlet port 14. A return spring tends to open the flow path so that flow is from the inlet 12 to the outlet 14. Moreover, pressure in this passage forces the valve element 26 to the right and thereby opens the manual push valve 20. The valve is sustained open (with or without the spring) by this pressure. This inevitably directs the fluid flow to the outlet port 14 except when overcome by push valve operation.

The cylinder head 16 is drilled at the top end and receives in a threaded connection the lower end of a cylindrical sleeve 30. The sleeve 30 is externally threaded and captures a seal 32 at the lower end. There is a reducer sleeve 34 within the cylinder 30 locked in location by means of an outwardly protruding lip 36. The lip 36 is captured beneath the lower end of the sleeve 30. The reducer sleeve 34 has an axial bore of specified diameter. This diameter is sized; it is sized to enable the device to accumulate sample at a different volume depending on scale. If the cross-sectional area of the passage in the reducer sleeve is quite large, a large volume of sample can be accumulated. On the other hand, if the passage that is drilled through the apparatus is quite narrow, then there is little accumulation. This is a scale factor which can be converted at the convenience of the user.

The reducer sleeve 34 surrounds a piston 38. The piston 38 is attached to a piston rod 40. The rod 40 extends upwardly and through the top end of the cylinder as will be described. The rod 40 supports a piston stop 42. It is a loose, telescoped sleeve around the piston rod 40. It limits the upward travel of the piston 38.

The sleeve 30 terminates at an upper piston head 46. The head is axially drilled to enable the piston rod 42 to extend through the drilled passage. As will be understood, seals surround the piston rod prevent leakage along the piston rod. The cylinder head 46 receives an adapter plug 48. The plug 48 is threaded into a counterbored opening, and has external threads thereon to fasten to a hollow, open cylindrical housing 50. The housing cooperates with a piston follower 52. The follower 52 has a sharp edge around the periphery to align against a set of calibration markings 54. They are incorporated as a convenience to the user to indicate scale. Preferably, the housing 50 is formed of transparent material with calibration marks embossed on it. The piston follower functions as a knife edge to define a volumetric level utilizing the embossed calibration marks. The housing 50 is a hollow tubular member preferably encircled by markings to enable the indicated quantity to be read from all sides. The follower 52 is full circle; it has an edge fully around the circumference.

The cylinder head 48 is drilled with a passage at 56 which connects with a valve 58. The valve 58 is normally closed. This enables the chamber 60 to be filled with an inert gas such as nitrogen. The inert gas fills the chamber to sustain back pressure on the piston 38. The gas forces the piston downwardly; this opposes the lifting force beneath the piston resulting from the sample captured below the piston 38.

Operation of the manual push valve 20 will be first described. Thereafter, operation of the device in the accumulation of sample will also be described. In the illustrated position, any fluid under pressure which is introduced through the port 12 flows through the port 14 and on to other equipment. This maintains the present apparatus 10 switched out of the system. No sample is introduced beneath the piston 38. Preferably, the pressure in the chamber 60 is maintained sufficiently high that the piston 38 is held in the down position. As an easy example, if the surges of pressure which accompany the taking of samples do not exceed 500 psi, then the pressure in the chamber 60 is maintained at about 750 psi; of course, the equipment can be rated much higher to sustain a higher pressure. Whatever the fact, this accumulated high pressure secures the piston in the down position, a position which indicates that there is no sample in the system. This fact is shown at the piston follower 52. The knife edge which is located around the periphery is aligned relative to the calibration marks 54 to indicate that no sample has been accumulated.

By hand operation the manual push valve 20 is closed. This locates the point of the valve element 26 in the constricted passage 28, and thereby diverts flow upwardly. As pressure surges occur with the taking of subsequent samples, they are delivered below the piston 38. The sample accumulates below the piston 38. The piston 38 is moved upwardly. As the piston 38 moves upwardly, its range of travel is limited by the sleeve 42 which serves as a piston stop. As sample is accumulated, the piston moves upwardly and slightly increases the pressure within the chamber 60. The rate of increase is limited in part by the relative size of the chamber 60 so that the increase is modest. Moreover, movement of the piston 38 is accompanied by movement of the piston rod 40. This moves the knife edge adjacent to the scale 54, thereby registering an indication of sample. Through suitable scale factors, the amount of sample can be determined using the calibrated marks which are visible on the exterior.

An important factor to note is the utilization of a removal reducer sleeve 34, piston 38 and piston stop sleeve 42. The various dimensions can be changed, thereby changing the capacity of the system. For instance, if the piston 38 has an increased diameter, it requires more sample to force it upwardly through a selected distance. This of course will be reflected by change of scale factors at the calibrations 54. In an alternate manner, the piston 38 can be reduced in size to provide an entirely different scale factor. Another alternate is use of longer or shorter piston stop sleeves.

This apparatus particularly enables volumetric scale changes. It is accomplished in the following manner. Matched sets of sleeves 34 and pistons 38 are provided for this purpose.

The device can be discharged simply by releasing the manually operated valve 20. This valve, on release, directs flow out of the area below the piston and out through the port 14. This flow is achieved at a rate dependent on the rate at which the downstream apparatus will accept the flow and it is urged from the apparatus by means of the pressure acting on the top of the piston. For this reason, the pressure above the piston is maintained at some relatively high level, and the pressure is not reduced below some set level during operation. The chamber pressure does increase above the piston as the volume of sample accumulates. Pressure in the chamber assures that the measured sample is then ejected when the manual push valve 20 is released.

While the foregoing is directed to the preferred embodiment, the scope is determined by the claims which follow.

What is claimed is:

1. A pressurized pumped pulsating sample accumulator for connection downsteam from a source accumulating samples delivered over a period of time, comprising:
   (a) a body having:
      (1) an inlet port;
      (2) an outlet port;
      (3) a passage between said ports;
      (4) a valve element;
      (5) a valve seat in said passage conforming to said valve element to close said passage to flow to said outlet port;
      (6) a second passage connected so that flow is diverted by said valve element to said second passage;
   (b) a hollow closed sleeve supported by said body;
   (c) a reducer sleeve located in said hollow sleeve and having a volumetric capacity of specified size;
   (d) a piston in said reducer sleeve, said piston closing said reducer sleeve and defining in said reducer sleeve a sample storage chamber;
   (e) said reducer sleeve being located to introduce sample through said second passage into said sample storage chamber;
   (f) an elongate rod connected to said piston and movable thereby;
   (g) calibrated indicator means supported by said closed sleeve and externally located to be viewed by a user to indicate volume within said reducer sleeve in said sample storage chamber; and (h) said sample storage chamber accumulating sample to move said piston and thereby move said rod, said rod operatively cooperative with said indicator means to form an indication of sample volume with said indicator means.

2. The apparatus of claim 1 including a cylinder head closing said closed sleeve and having a passage therethrough to enable said rod to extend through said head to an external location, and said head further defining a closed chamber for receiving a pressure fluid acting against said piston, said piston being urged thereby toward a position achieved with no sample in said sample storage chamber.

3. The apparatus of claim 2 including piston stop means limiting travel of said piston on accumulating sample.

4. The apparatus of claim 3 wherein said piston stop means comprises an elongate sleeve around said rod, said stop means limiting movement of said piston toward said cylinder head and further being replacable with an alternate length piston stop sleeve.

5. The apparatus of claim 1
(a) wherein said valve element is supported on a valve stem of specified length, said stem extending toward the exterior of said body;
(b) a coil spring around said stem;
(c) means connecting said coil spring to said stem;
(d) means cooperative with said stem for urging said stem in a direction causing said valve element to close against said valve seat against said coil spring; and
(e) means for reducing said stem for moving said valve element away from said valve seat.

6. The apparatus of claim 4
(a) wherein said valve element is supported on a valve stem of specified length, said stem extending toward the exterior of said body;
(b) a coil spring around said stem;
(c) means connecting said coil spring to said stem;
(d) means cooperative with said stem for urging said stem in a direction causing said valve element to close against said valve seat against said coil spring; and
(e) means for reducing said stem for moving said valve element away from said valve seat.

7. The apparatus of claim 6 including a hand operable external push button on said stem.

8. The apparatus of claim 1 including:
(a) an upstanding transparent calibrated member adjacent to said rod;
(b) a marker carried on said rod adjacent to said member for indicating rod movement; and
(c) means for selectively demounting said member to enable replacement with an alternative member having an alternate calibration thereon.

9. The apparatus of claim 6 including:
(a) an upstanding transparent calibrated member adjacent to said rod;
(b) a marker carried on said rod adjacent to said member for indicating rod movement; and
(c) means for selectively demounting said member to enable replacement with an alternative member having an alternate calibration thereon.

10. The apparatus of claim 8 wherein said calibrated member comprises an upstanding hollow cylindrical member of transparent material, and said marker comprises a sharp edge adjacent to said transparent member to indicate sample volume against said trandparent member.

11. The apparatus of claim 9 wherein said calibrated member comprises an upstanding hollow cylindrical member of transparent material, and said marker comprises a sharp edge adjacent to said transparent member to indicate sample volume against said transparent member.

* * * * *